US010582887B2

(12) United States Patent
O'Donnell et al.

(10) Patent No.: US 10,582,887 B2
(45) Date of Patent: Mar. 10, 2020

(54) BLOOD OXYGENATION SENSOR WITH LED CURRENT MODULATION

(71) Applicant: Analog Devices Global, Hamilton (BM)

(72) Inventors: John Jude O'Donnell, Quin (IE); Javier Calpe Maravilla, Algemesi (ES); Colin G. Lyden, Baltimore (IE); Thomas G. O'Dwyer, Arlington, MA (US)

(73) Assignee: Analog Devices Global, Hamilton (BM)

( * ) Notice: Subject to any disclaimer, the term of this patent is extended or adjusted under 35 U.S.C. 154(b) by 397 days.

(21) Appl. No.: 15/072,961

(22) Filed: Mar. 17, 2016

(65) Prior Publication Data

US 2017/0265794 A1 Sep. 21, 2017

(51) Int. Cl.
*A61B 5/1455* (2006.01)
*A61B 5/0402* (2006.01)
*A61B 5/00* (2006.01)

(52) U.S. Cl.
CPC ........ *A61B 5/14552* (2013.01); *A61B 5/0402* (2013.01); *A61B 5/7292* (2013.01); *A61B 2562/0238* (2013.01)

(58) Field of Classification Search
CPC .............. A61B 5/1455; A61B 5/14551; A61B 5/14552; A61B 5/7285; A61B 5/7292; A61B 2562/02238
See application file for complete search history.

(56) References Cited

U.S. PATENT DOCUMENTS

| 4,911,167 | A | * | 3/1990 | Corenman | ......... | A61B 5/02416 |
| | | | | | | 600/324 |
| 5,313,941 | A | * | 5/1994 | Braig | ................. | A61B 5/14532 |
| | | | | | | 600/316 |

(Continued)

FOREIGN PATENT DOCUMENTS

CN 1929777 A 3/2007
CN 101627902 A 1/2010
(Continued)

OTHER PUBLICATIONS

Martin-Martinez, Diego, et al., "Stochastic Modeling of the PPG Signal: A Synthesis-by-Analysis Approach with Applications", IEEE Transactions on Biomedical Engineering, 60(9), (Sep. 2013), 2432-2441.

(Continued)

*Primary Examiner* — Eric F Winakur
(74) *Attorney, Agent, or Firm* — Schwegman Lundberg & Woessner, P.A.

(57) ABSTRACT

A blood oxygenation sensor is provided comprising: a first current-powered light source to produce light having a first wavelength; a second current-powered light source to produce light having a second wavelength; a light sensor to produce a current signal having a magnitude that is indicative of intensity of light incident upon it; a current level driver circuit that includes a current source configured to couple the current source to alternatively provide current to one of the first current-powered light source and the second light current-powered light source; a processor configured to predict times of occurrence of one or more first time intervals in which arterial volume at a tissue site is at one of a maximum and a minimum; wherein the processor is configured to control the current source, to provide a first pattern of higher power-dissipation current pulses to the first and second current-powered light sources during the first (Continued)

time intervals, and to provide a second pattern of lower power-dissipation current pulses to at least one of the first and second current-powered light sources during second time intervals.

19 Claims, 17 Drawing Sheets

(56) References Cited

U.S. PATENT DOCUMENTS

| | | | |
|---|---|---|---|
| 6,697,658 B2* | 2/2004 | Al-Ali | A61B 5/1455 600/323 |
| 7,162,288 B2* | 1/2007 | Nordstrom | A61B 5/14551 600/323 |
| 8,457,703 B2 | 6/2013 | Al-Ali | |
| 9,241,676 B2* | 1/2016 | Lisogurski | A61B 5/14551 |
| 2007/0208240 A1 | 9/2007 | Nordstrom et al. | |
| 2011/0029247 A1* | 2/2011 | Kalathil | A61B 5/14551 702/19 |
| 2013/0324856 A1 | 12/2013 | Lisogurski et al. | |
| 2016/0143566 A1* | 5/2016 | Ballam | A61B 5/14552 600/323 |

FOREIGN PATENT DOCUMENTS

| | | |
|---|---|---|
| CN | 102440786 A | 5/2012 |
| CN | 104968267 A | 10/2015 |
| CN | 107198529 | 9/2017 |
| EP | 1722674 B1 | 4/2008 |
| WO | WO-2012099538 A1 | 7/2012 |

OTHER PUBLICATIONS

Gubbi, Sagar Vankatesh, et al., "Adaptive Pulse Width Control and Sampling for Low Power Oximetry", IEEE Transaction on Biomedical Circuits and Systems, vol. 9, No. 2, (Apr. 2015), 12 pgs.

"Chinese Application Serial No. 201710158405.1, Office Action dated Jul. 29, 2019", w/ English translation, 29 pgs.

* cited by examiner

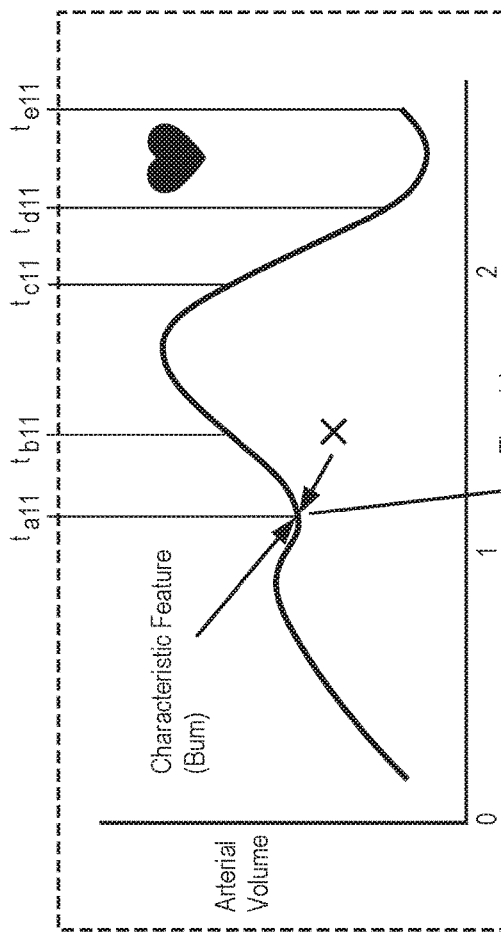
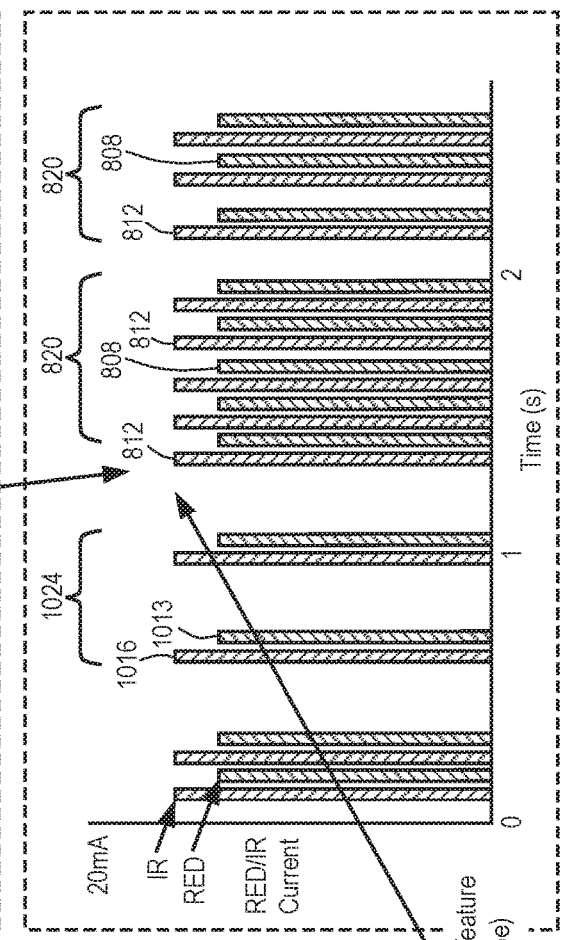
FIG. 11A
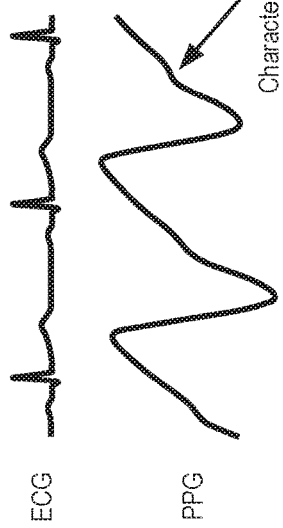
FIG. 11B

BLOOD OXYGENATION SENSOR WITH LED CURRENT MODULATION

BACKGROUND

A pulse oximeter sensor measures the percentage oxygen saturation in arterial hemoglobin, which indicates percentage of hemoglobin molecules in the arteries that contain an oxygen molecule. This measurement also is commonly referred to as saturation of peripheral oxygen, or as $SpO_2$. FIG. 1 is an illustrative drawing representing blood oxygenation levels in an artery. In this illustrative example, seventy-five per cent of the blood hemoglobin molecules are oxygenated ($HbO_2$) and twenty-five percent of the blood hemoglobin molecules are deoxygenated (Hb).

Oxygenated and deoxygenated blood have different absorption levels for red and infrared (IR) light. FIG. 2 is an illustrative drawing representing the difference in absorbance levels of two different light wavelengths in the red and IR bands, by oxygenated hemoglobin and deoxygenated hemoglobin. The ratio of the absorbance of oxygenated hemoglobin to deoxygenated hemoglobin is lower in the red portion of the spectrum than it is in the IR portion of the spectrum. In other words, Hb absorbs red light more readily than $HbO_2$, and $HbO_2$ absorbs IR light more readily than Hb.

A typical pulse oximeter operates by directing red light emitted by a red LED and IR light emitted by an IR LED onto a patient's body tissue, and measuring the intensity of red and IR light that passes through the tissue medium and is detected by a photodector. The relative intensities of red and IR light detected by the photodetector, and how those intensities vary in response to the heartbeat pulse, provide a measure of blood oxygenation level.

Arterial volume changes in a periodic pattern in response to blood pressure variations during a heartbeat. FIG. 3 is an illustrative waveform showing a typical periodic pattern of the detected light which correlate with the changes in arterial volume during a sequence of blood pressure pulses within an artery and also showing corresponding representations of maximum and minimum arterial volumes that occur during each pressure pulse. During a systole phase of a heart beat activity, when arterial pressure is at a maximum, arterial volume and arterial diameter are at a maximum so there is more arterial blood flow and thus more light is absorbed and then, less light arrives to the photodetector. During a diastole phase of a heart beat activity, when arterial pressure is at a minimum, arterial volume and arterial diameter are at a minimum. Thus, the red and IR wavelengths absorbed by the artery has an AC pulsatile characteristic that can be isolated from the DC absorption characteristic of other components, such as tissue, non-pulsatile arterial blood, venous blood, skin reflection or even stray light, for example, whose volume does not vary in periodic pattern. A pulse oximeter sensor typically utilizes the periodic time varying nature of arterial volume to distinguish red and IR light absorption by oxygenated and deoxygenated hemoglobin within the blood from red and IR light absorption by other components and tissues surrounding or adjacent to the artery such as muscle, nerve, fat, or connective tissue, for example.

In the past, to measure both red light absorption and IR light absorption during each heartbeat, a red LED and an IR LED have been alternately turned on and off to produce alternating pulses of red and IR light. A photodiode detects alternating pulses of red and IR. light that have passed through the arteries, arterioles, and capillaries that transport arterial blood. Very often the light penetrates in the tissue but does not really get to the artery. Rather, it diffuses though the capillaries closer to the skin which have a similar (but softer) behaviors to what has been described for arteries. SpO2 level is determined based upon both the average (constant) and pulsatile (that which varies in response to the heartbeat) relative-intensities of red and IR radiation detected. FIGS. 4A-4B are illustrative waveforms 402, 404 representing typical evolution of arterial volume during a sequence of blood pressure pulses within an artery (FIG. 4A) and an alternating sequence of current flow pulses in a red LED and an IR LED turn-on signals (FIG. 4B) to alternately turn-on the red LED and the IR LED. A sequence of first current pulses 408 having a first current value are provided during a sequence of first time intervals to turn-on the red LED during each of the first time intervals. A sequence of second current pulses 410 having a second current value are provided during a sequence of second time intervals to turn-on the IR LED during each of the second time intervals. The first time intervals and the second time intervals are interleaved so that the red LED and the IR LED take turns, or alternate, turning on to produce an alternating sequence of red and IR light pulses. Photodetector measurements of the diffused light produced by the red and IR LEDs are processed to determine red and IR light absorption levels.

FIG. 5A is an illustrative drawing showing a first pulse oximetry system 500 that is powered from an external power source. The first system 500 includes a housing 502 that encloses a pulse oximetry sensor (not shown). In operation, the housing is mounted on a patient's finger to position the sensor to take pulse oximetry measurements. A wire 504 couples the sensor with signal processing circuity 506 that includes a user interface screen 507 to display pulse oximetry measurements. The sensor sends signals over the wire 504 to the processing circuitry 506 that are indicative of red light intensity and IR light intensity incident upon a photo-diode (not shown). The wire also provides power to the sensor from the external power source. The sensor also receives LED control signals over the wire 504 from the processing circuitry 506 to control the intensity of light emitted by the red and IR LEDs, The processing circuity 506 is mounted on a portable work station 508.

FIG. 5B is an illustrative drawing showing a second pulse oximetry system 520 that is battery powered. The second system 520 includes a housing 522 that encloses a pulse oximetry sensor (not shown). In operation, the housing 522 is mounted on a patient's finger so as to position the sensor to take pulse oximetry measurements. A wire 524 couples the sensor with a battery powered smart watch 526 that includes a user interface screen 527 configured to display pulse oximetry measurements. The wire also provides power to the sensor from the watch battery (not shown). The smart watch 526 receives signals indicative of light intensity, performs signal processing, displays measurement results, sends control signals and is mounted on the patient's wrist.

FIG. 5C is an illustrative drawing showing a third pulse oximetry system 540 that is battery powered. The third system 540 includes a housing 542 that encloses a pulse oximetry sensor (not shown), built-in processing circuitry (not shown), a built-in display screen configured to display pulse oximetry measurements, and a battery (not shown). In operation, the housing 542 with its associated sensor, processing circuity, and display screen 547, are mounted on a patient's finger to position the sensor to take pulse oximetry measurements.

FIG. 5D is an illustrative perspective view of a fourth blood oximeter sensor system 560 that is battery powered. The fourth system 560 includes a housing 562 that encloses a pulse oximetry sensor (not shown). The sensor system 560 communicates wirelessly via RF transmissions 570 with an external processing system 566 that includes a display screen 567 to display blood oximetry measurements.

SUMMARY

In one aspect, a blood oxygenation sensor is provided. A first current-powered light source produces light having a first wavelength. A second current-powered light source produces light having a second wavelength. A light sensor produces a current signal having a magnitude that is indicative of intensity of light incident upon it. A current level driver circuit includes a current source configured to couple the current source to alternatively provide current to the first or second current-powered light sources. A processor system is configured to predict times of occurrence of one or more first time intervals in which arterial volume at a tissue site is at one of a maximum and a minimum based at least in part upon magnitude of current stimulated by the light sensor in response to light that has been transmitted through the tissue site and that is incident upon the light sensor during one or more second time intervals in which the arterial volume at the tissue medium site is between the minimum and maximum values. The processor system is configured to control the current source to provide a first pattern of higher power-dissipation current pulses to the first and second current-powered light sources during the first time intervals, and to provide a second pattern of lower power-dissipation current pulses to at least one of the first and second current-powered light sources during second time intervals between the first time intervals.

In another aspect, a method is provided for use with a blood oxygenation sensor that includes LED circuitry and a photodiode. A first pattern of higher power-dissipation current pulses is provided to the LED circuitry during time intervals while an arterial volume at a tissue medium site is at a maximum and during first time intervals while the arterial volume at the tissue medium site is at a minimum. A second pattern of lower power-dissipation current pulses is provided to the LED circuitry during second time intervals while the arterial volume at the tissue medium site is between minimum and maximum values. A blood oxygenation measurement is determined based at least in part upon current stimulated in the photodiode in response to light that is emitted by the LED circuitry in response to the first pattern of current pulses and that passes through the tissue medium site before reaching the photodiode. Times of occurrence of the arterial volume maximums and minimums are predicted based at least in part upon current stimulated in the photodiode in response to light that is emitted by the LED in response to the second pattern of current pulses and that is transmitted through the tissue medium site before reaching the photodiode.

BRIEF DESCRIPTION OF THE DRAWINGS

FIGS. 11A-11B are illustrative drawings representing arterial pressure during a sequence of blood pressure pulses within an artery (FIG. 11A) and an alternating sequence of LED current values (FIG. 11B) that pulse at different at different pulse rate frequencies in response to an arterial volume waveform morphology in accordance with some embodiments.

DESCRIPTION OF EMBODIMENTS

Figure 1:
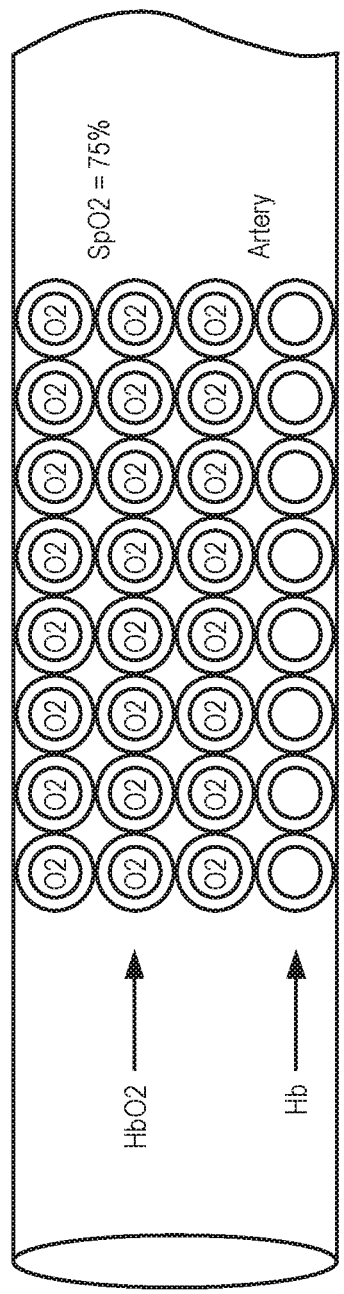
FIG. 1 is an illustrative drawing representing blood oxygenation levels in an artery.
Figure 2:
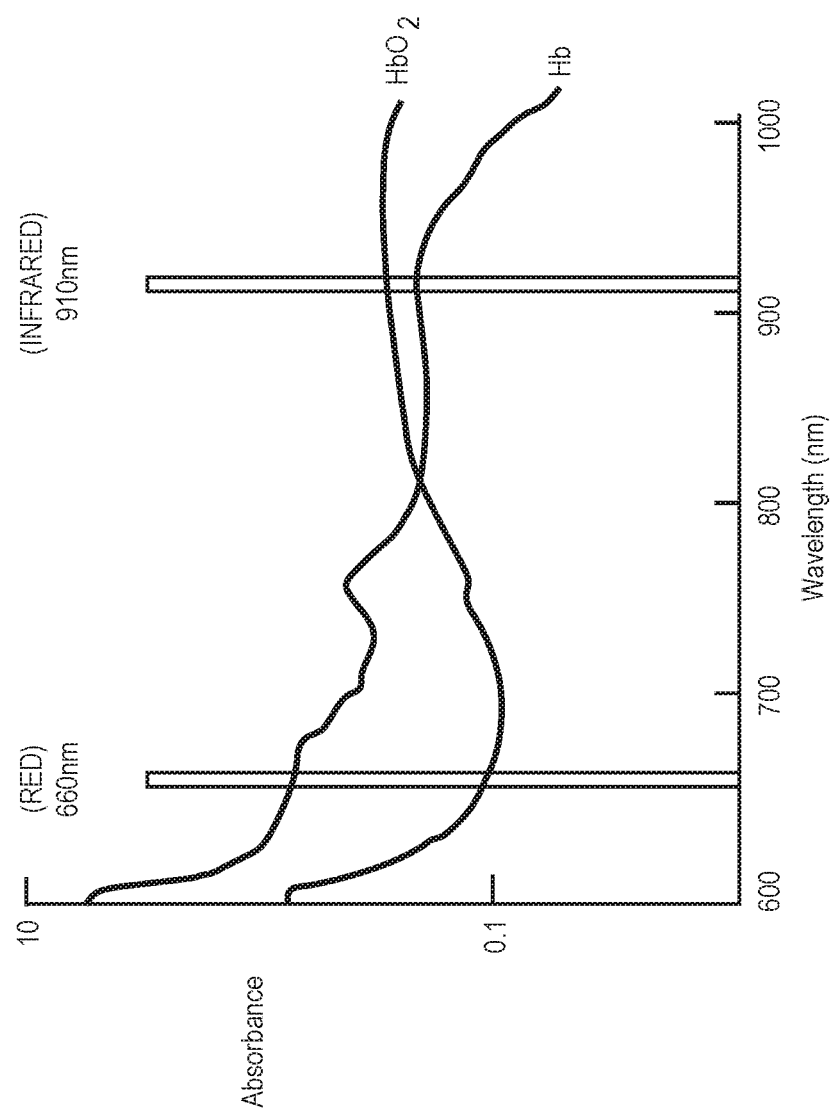
FIG. 2 is an illustrative drawing representing a difference in absorption of red and IR light by oxygenated hemoglobin and deoxygenated hemoglobin.
Figure 3:
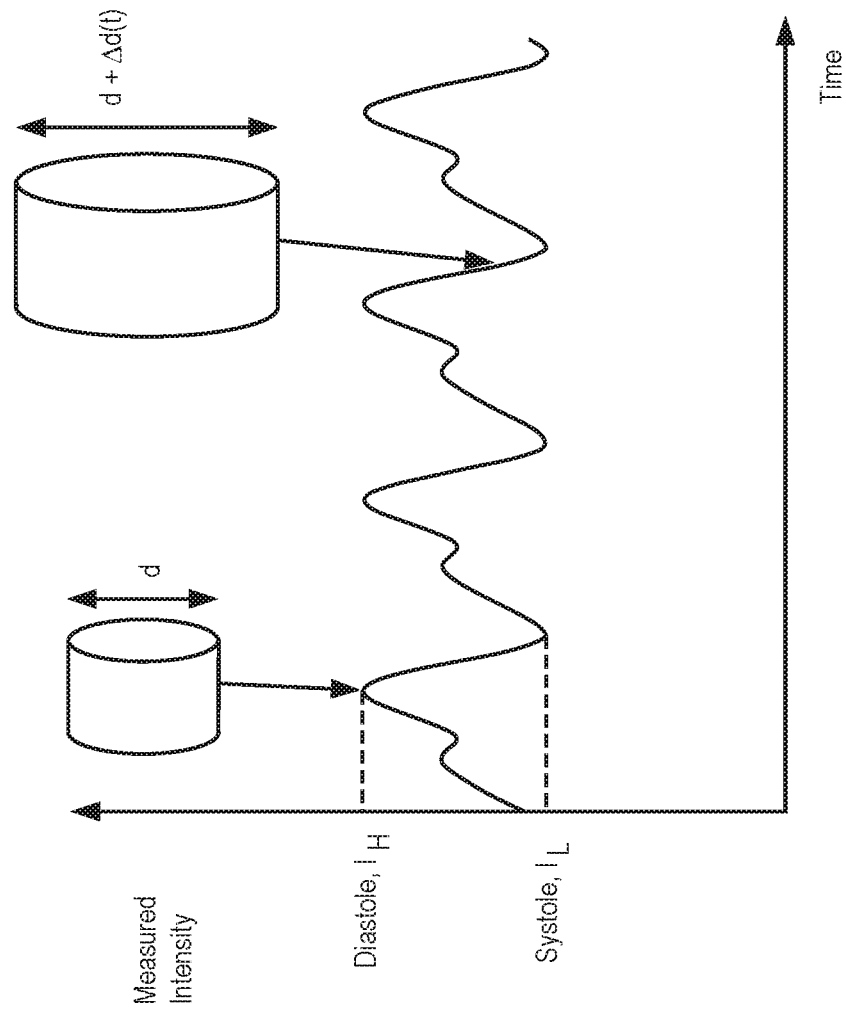
FIG. 3 is an illustrative curve representing typical transmitted light intensity during a sequence of blood pressure pulses within an artery and showing corresponding changes in arterial volume in response to the variations in light absorption.
Figure 4A:
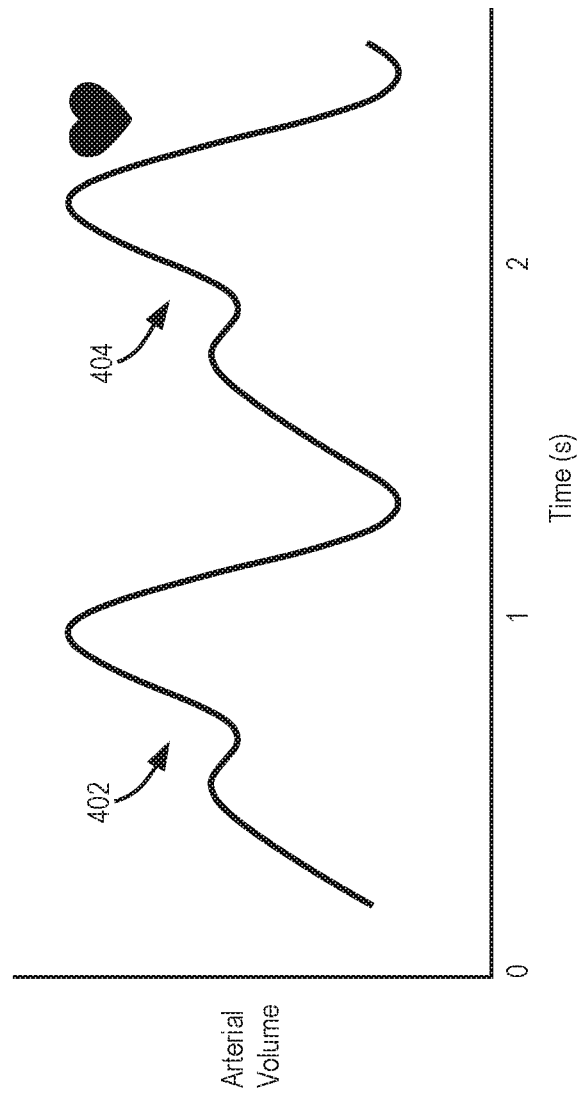
FIGS. 4A-4B are illustrative waveforms representing typical evolution of arterial volume during a sequence of blood pressure pulses within an artery (FIG. 4A) and an alternating sequence of current flow pulses in a red LED and an IR LED turn-on signals (FIG. 4B).
Figure 4B:
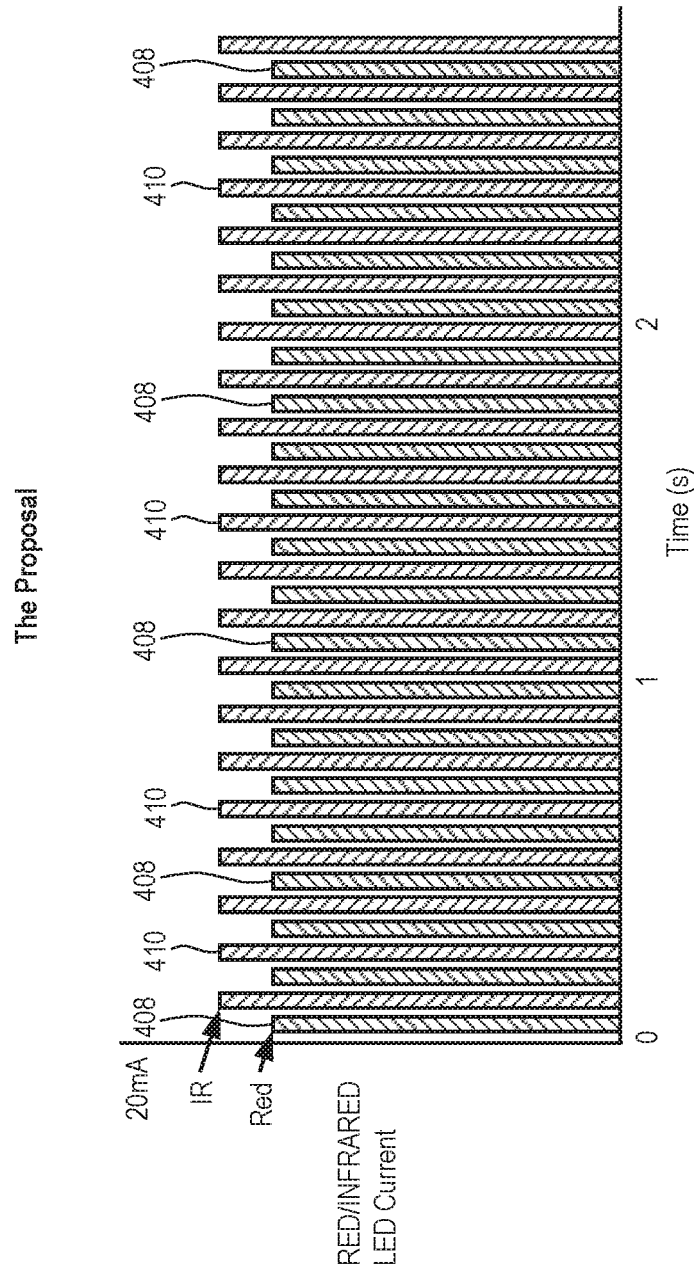
Figure 5A:
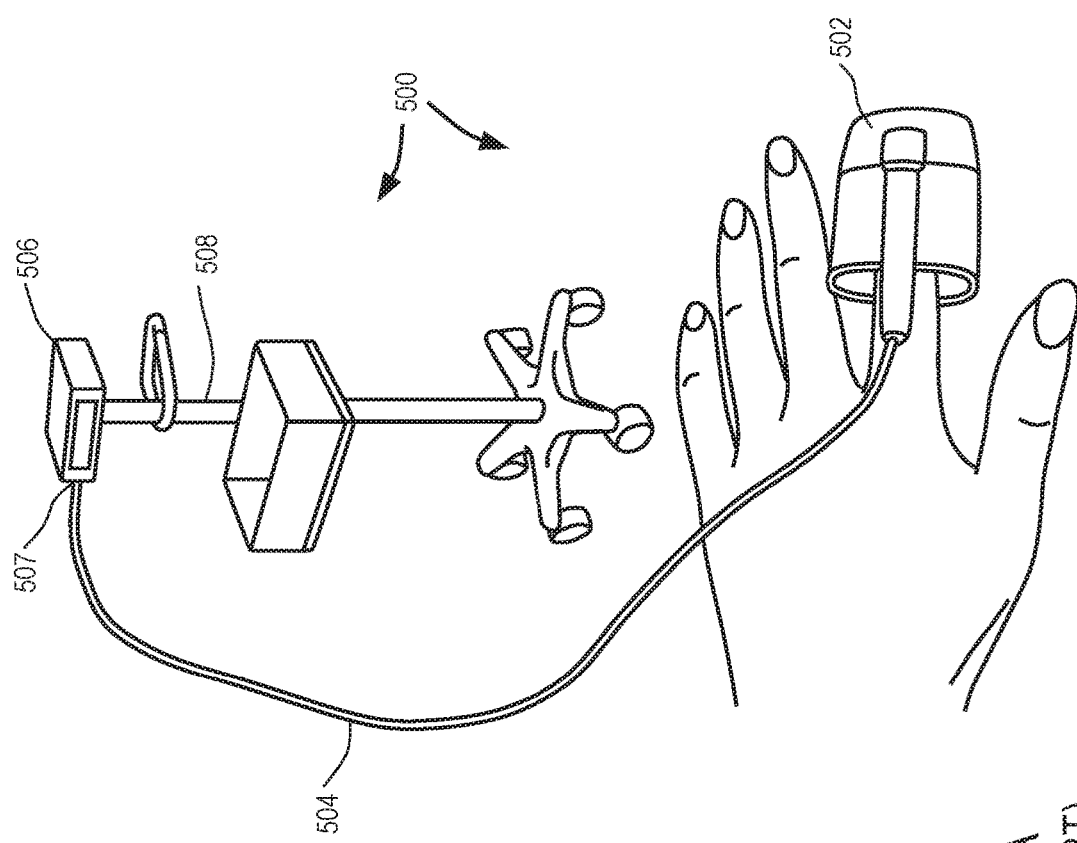
FIG. 5A is an illustrative drawing showing a first pulse oximetry system that is powered from an external power source.
Figure 5B:
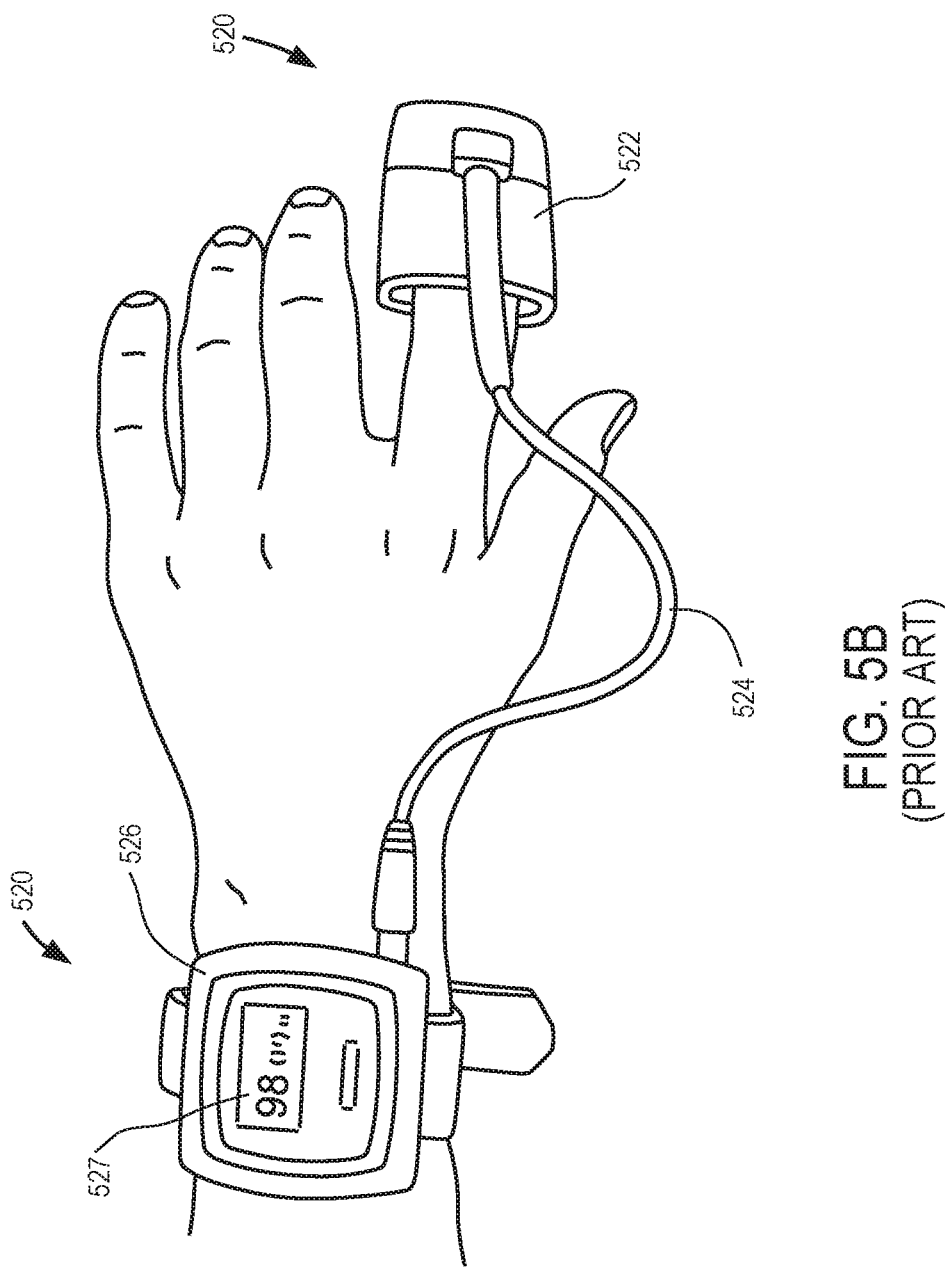
FIG. 5B is an illustrative drawing showing a second pulse oximetry system that is powered and supported by a wrist-worn smartwatch that includes a battery unit.
Figure 5C:
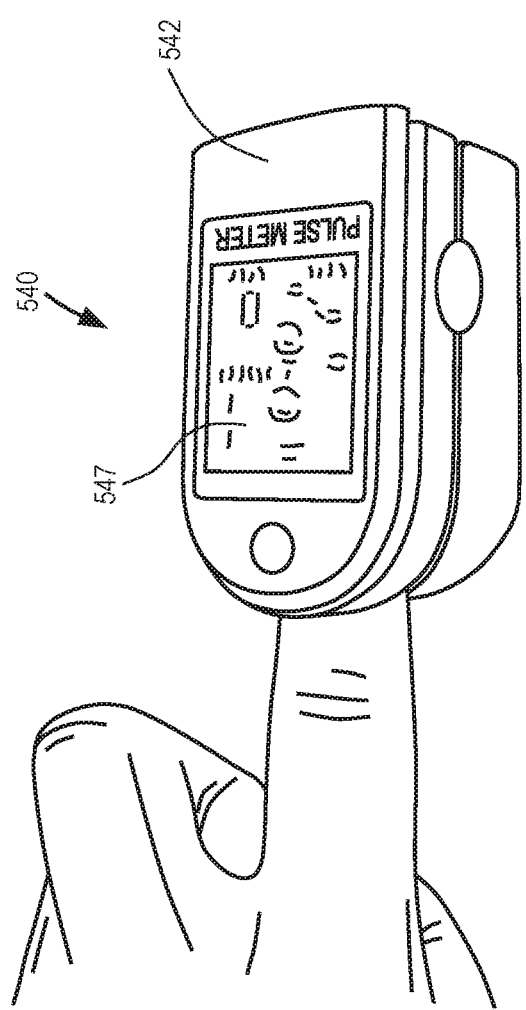
FIG. 5C is an illustrative drawing showing a third pulse oximetry system that powered from a self-contained battery and which also contains a display for communicating SpO2 measurements.
Figure 5D:
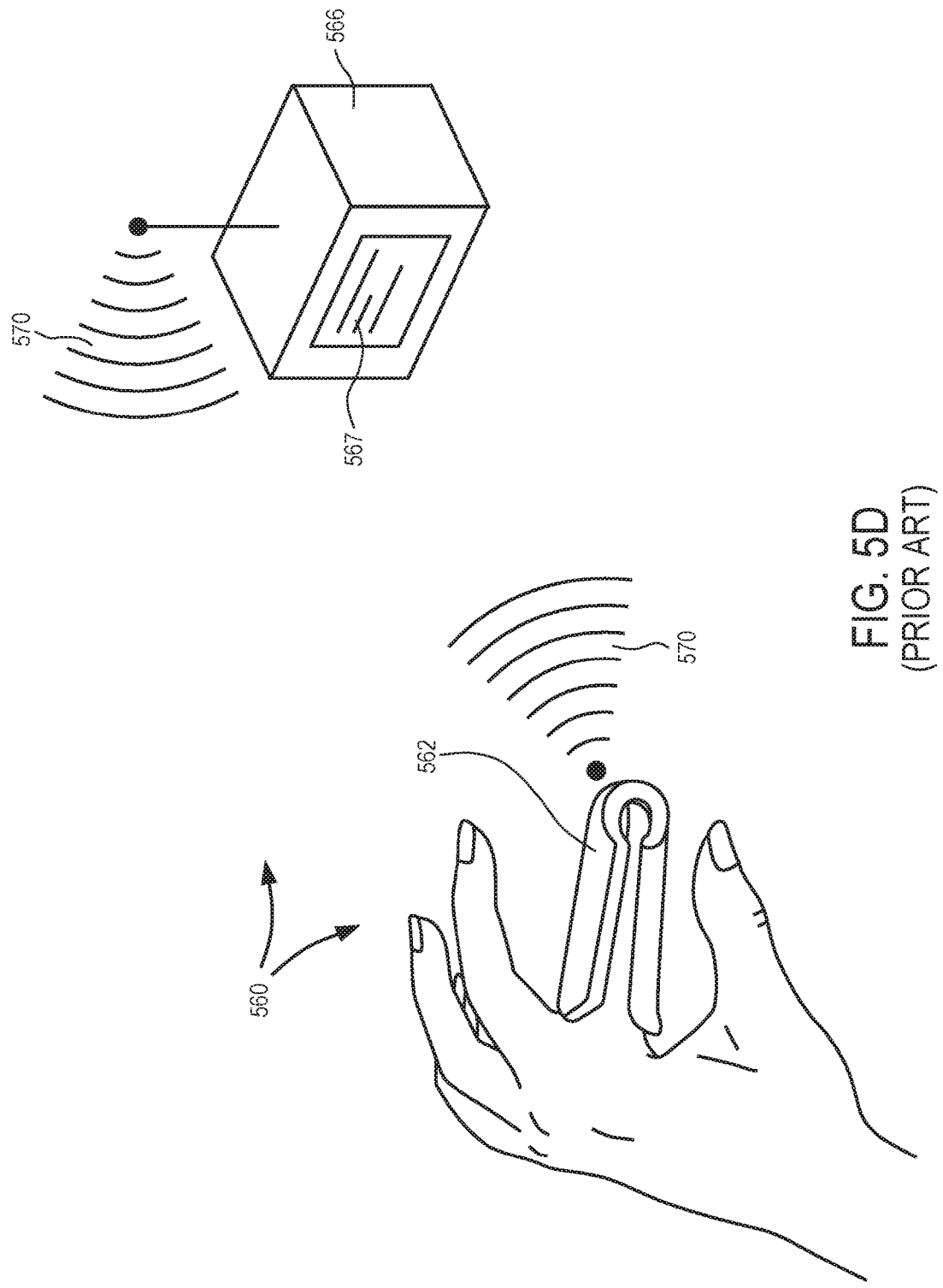
FIG. 5D is an illustrative drawing showing a fourth pulse oximetry system that is battery powered and which has a built-in radio for communication of SpO2 measurements to a remote unit.

The following description is presented to enable any person skilled in the art to create and use a pulse oximeter sensor with LED current modulation. Various modifications to the embodiments will be readily apparent to those skilled in the art, and the generic principles defined herein may be applied to other embodiments and applications without departing from the spirit and scope of the invention. Moreover, in the following description, numerous details are set forth for the purpose of explanation. However, one of ordinary skill in the art will realize that the invention might be practiced without the use of these specific details. In other instances, well-known processes are shown in block diagram form in order not to obscure the description of the invention with unnecessary detail. Identical reference numerals may be used to represent different views of the same or similar item in different drawings. Flow diagrams in drawings referenced below are used to represent processes. Thus, the present invention is not intended to be limited to the embodiments shown, but is to be accorded the widest scope consistent with the principles and features disclosed herein.

Figure 6A:
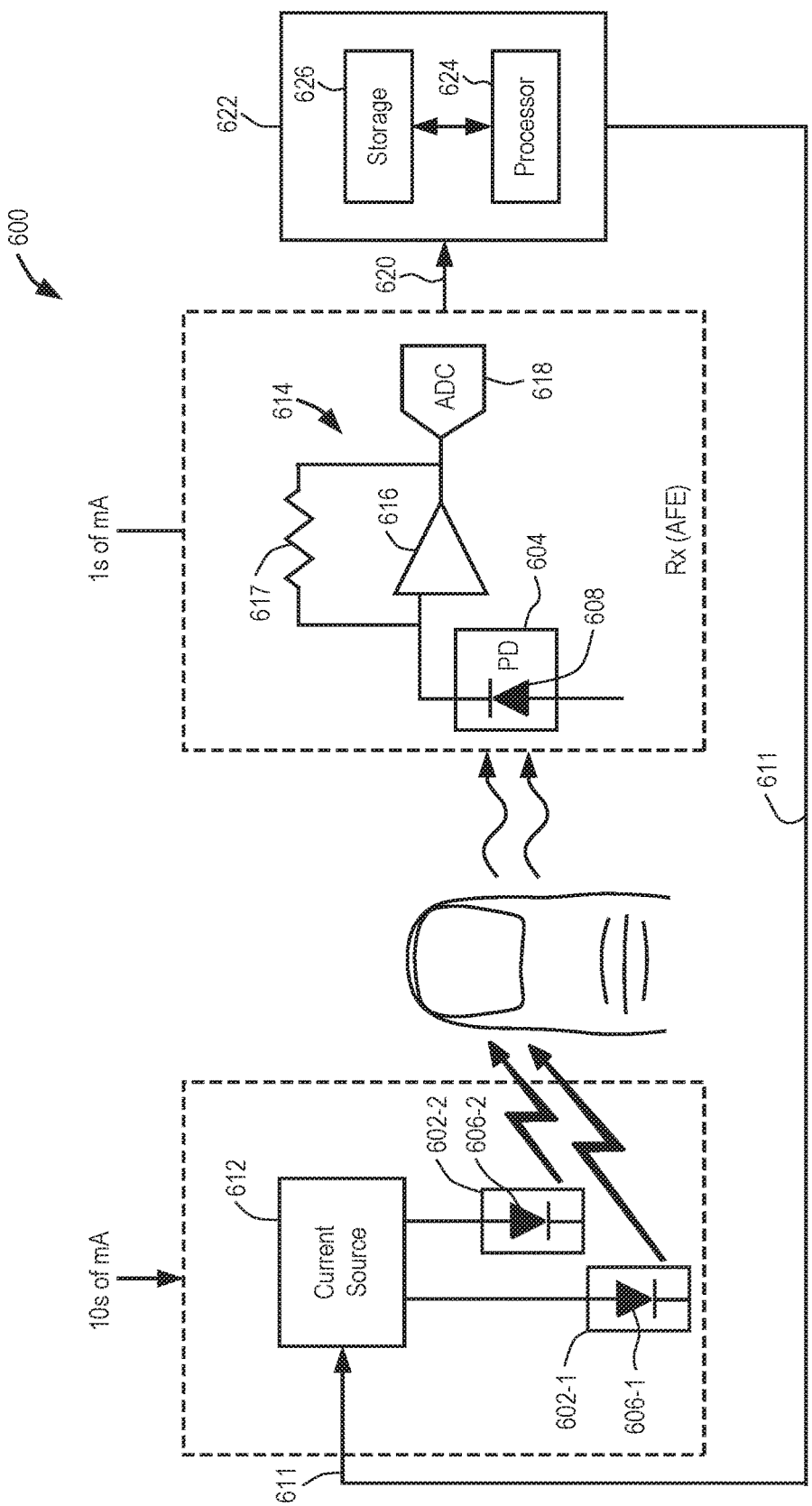
FIG. 6A is an illustrative schematic block diagram showing certain details of a pulse oximeter circuit system in accordance with some embodiments.

FIG. 6A is an illustrative schematic block diagram showing certain details of a pulse oximeter sensor system 600 in accordance with some embodiments. The sensor system 600 includes first and second light sources 602-1, 602-2, and a photodetector 604. The first light source 602-1 includes a first light emitting diode (LED) 606-1 that emits light at a first light wavelength. The second light source 602-2 includes a second light emitting diode (LED) 606-2 that emits light at a second light wavelength. In some embodiments the first light wavelength includes red light, and the second light wavelength includes the infrared (IR) light. The photodetector 604 includes a photodetector diode 608. The control signal on line 611 controls current flows within the first and second LEDs 606-1, 606-2. The current level driver circuit 612 drives the first and second LEDs 606-1, 606-2. A transimpedance (TIA) amplifier circuit 614, which includes amplifier circuit 616 and resistor 617 is coupled to act as a current-to-voltage converter to convert current signals stimulated in the photodetector diode 608 in response to light incident upon it to corresponding voltage signals. The photodetector current value is proportionate to and representative of intensity of light incident upon the photodetector diode 608. An ADC circuit 618 converts the voltage signal representing light intensity incident upon the photodetector diode 608 from an analog to a digital representation and provides on line 620 a digital signal representation of the light intensity incident upon the photodetector diode 608. A signal processing module 622 includes a processor circuit 624 and an associated hardware storage 626, which are operatively coupled to communicate information between them. The signal processing module 622 receives the digital signal provided on line 620 and provides the digital control signal on line 611 as a feedback signal to the DAC circuit 610.

Figures 6B, 6C:
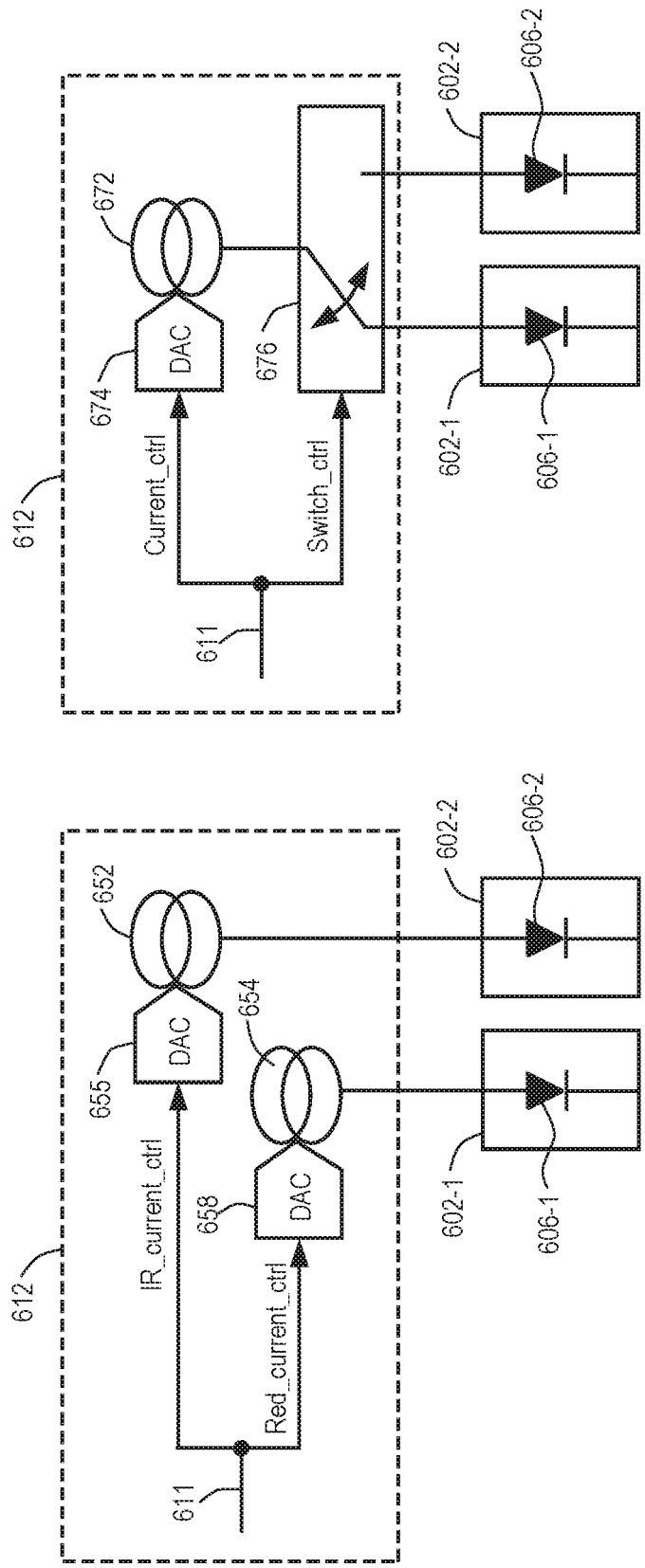
FIG. 6B is an illustrative drawing showing certain details of a first embodiment of the current source of FIG. 6A.
FIG. 6C is an illustrative drawing showing certain details of a second embodiment of the current source of FIG. 6A.

FIG. 6B is an illustrative drawing showing certain details of a first embodiment of the current source 612 of FIG. 6A. The first embodiment of the current source 612 includes multiple internal current sources 652, 654. A first internal current source 652 that is coupled to supply current to the first light source 602-1 and includes a second internal current source 654 that is coupled to supply current to the second light source 602-2. A first DAC 656 is coupled to receive the digital control signal on line 611, to convert the digital signal to an analog signal and to provide a corresponding analog control signal to control operation of the first internal current source 652. A second DAC 658 is coupled to receive the digital control signal on line 611, to convert the digital signal to an analog signal and to provide a corresponding analog control signal to control operation of the second internal current source 654.

FIG. 6C is an illustrative drawing showing certain details of a second embodiment of the current source 612 of FIG. 6A. The second embodiment of the current source 612 includes an internal current source 672 and a switch, a DAC 676 and a switch 678 to selectably couple the current source 672 to either one of the first and second light sources 602-1, 602-2. The DAC 676 is coupled to receive the digital control signal on line 611, to convert the digital signal to an analog control signal and to provide the corresponding analog control signal to control operation of the current source 676. The switch 678 is coupled to receive switch control signals on line 611 to determine which of the light sources 602-1, 602-2 to couple to the current source 672.

In operation, the light sources 602-1, 602-2 and the photodetector 604 are placed in close proximity to an anatomical tissue site such that light emitted from the light sources 602-1, 602-2 is incident upon the site and so that light emitted from the light sources that passes through the tissue site is incident upon the photodetector 604. The example in FIG. 6A shows them disposed proximate to a finger 628, although they can be placed in close proximity to other body sites such as wrist, ear lobe, ear cavity, forehead etc. It will be understood that in the case of a finger or ear lobe, for example, light enters the tissue at an entry site, passes through the tissue medium, and exits the tissue at a different site disposed opposite the entry site. However, in the case of the forehead or even the finger, for example, light enters the tissue at an entry site, passes through the tissue medium, reflects off underlying bone or other tissue, or diffuses, passes through the tissue medium once again, and exits at or nearby the entry site.

More particularly, the light sources 602-1, 602-2 and the photodetector 604 are suitably positioned relative to a tissue site for blood oxygenation level measurements that provide an indication of blood oxygenation levels. In some embodiments, an $SpO_2$ sensor senses differences in the intensity of light of two different wavelengths emitted from the light sources 602-1, 602-2, e.g., red and IR, incident upon the photodetector 604 to evaluate the proportion of blood hemoglobin molecules in artery blood vessels that have an $O_2$ molecule attached. Also, the light sources 602-1, 602-2 and the photodetector 604 are suitably positioned relative to the tissue site for photoplethysmography (PPG) measurements that provide an indication of local arterial, arteriole, or capillary volume changes at the tissue site that are indicative of the occurrence of a heartbeat activity. More particularly, a PPG sensor detects blood pressure change, which is indicative of changes in arterial volume during passage of a blood pulse waveform caused by a heartbeat.

In its function sensing blood oxygenation level, the sensor system 600 detects a blood oxygenation level based upon a difference in blood's absorption of two different light wavelengths. Oxygenated hemoglobin molecules more readily absorb IR light. Deoxygenated hemoglobin molecules more readily absorb red light. Thus, the current levels stimulated in the photodetector diode 608 in response to both the RED and IR light passing through the tissue medium have information that is indicative of the proportion of oxygenated hemoglobin (HbO2) in the blood. Moreover, it is noted that the signal from the Red light contains information from both and the IR light contains information from both as well.

Blood oxygenation level can be determined based upon absorption of red light and IR light during occurrences of maximum and minimum arterial volumes. A process to determine blood oxygenation levels in accordance with some embodiments, receives, as inputs, the DC red light and DC IR light intensities as measured at the photodiode. The process also receives as input the magnitude of the AC component of the red and IR signals where AC is defined as the component of the signal which varies in response to the arterial volume variations. In general, these will be at the same frequency as the heartrate. The magnitude of that AC component can be determined based upon a measured light intensity at the maxima and minima of the AC component.

In some embodiments, the processor 624 is configured to determine blood oxygenation level (BOL) based upon the following formulation:

$$BOL = \text{a function of} [(I_{maxRed} - I_{minRed})/(I_{maxIR} - I_{minIR})]/[DC_{Red}/DC_{IR}] \quad (1)$$

Where, $I_{maxRed}$=Photodiode current received, during an occurrence of minimal arterial volume, in response to Red LED illumination of tissue; $I_{minRed}$=Photodiode current, during an occurrence of maximal arterial volume, in response to Red LED illumination of tissue; $I_{maxIR}$=Photodiode current, during an occurrence of minimal arterial volume, in response to IR LED illumination of tissue; $I_{minIR}$=Photodiode current, during an occurrence of maximal arterial volume, in response to IR LED illumination of artery; $DC_{Red}$=AveragePhotodiode current in response to Red LED illumination of non-pulsatile components; and $DC_{IR}$=Average Photodiode current in response to IR LED illumination of non-pulsatile components. Thus, it will be appreciated that the maximum and minimum photodiode currents are those measured as a result of the illumination of the whole tissue, not just the artery. It is in the difference between these currents that are isolated, not the just artery component, but the component of the artery contribution that is pulsing in response to the heartbeat.

The accuracy with which photodiode current level provides a measure of incident light intensity is dependent upon the intensity of that received light. In other words, the SNR of photodiode current within the photodiode 608 increases with increasing LED light intensity. The larger the current provided to the first and second light source LEDs 606-1, 606-2, the greater the intensity of the light they produce and the more accurately the resulting current stimulated in photodiode 608 represents the intensity of light that propagates through the tissue medium. However, increased LED current results in more rapid power dissipation, which is especially problematic in battery powered systems and also may saturate the AFE or may be too much in some case (think about light reflection from a finger of a fair complexion child as compared with light reflection from a darker complexion child).

In accordance with some embodiments, the red LED and the IR LED are turned on with a higher turn-on current during time intervals that encompass arterial waveform maxima and minima.

Figures 7A, 7B:
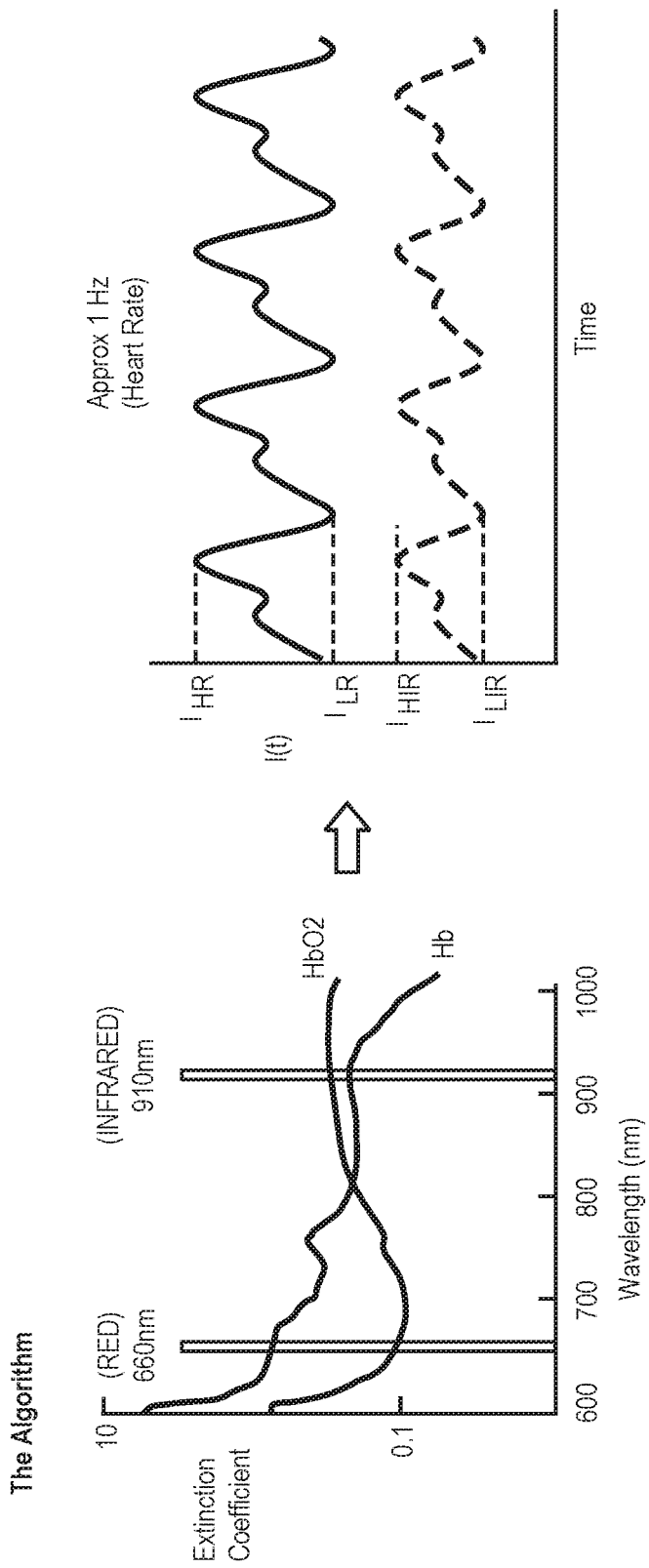
FIGS. 7A-7B is an illustrative plot showing relative absorption (extinction ratio) of Hb and HbO2 as a function of light wavelength (FIG. 7A) and a pair of plots of photodiode current in response to red and Infra-red stimulus (FIG. 7B).

FIGS. 7A is an illustrative plot showing relative absorption (extinction ratio) of Hb and HbO2 as a function of light wavelength. The vertical bands representing red absorption and IR absorption are shown. FIG. 7A is an illustrative pair of plots of photodiode current in response to red and Infra-red stimulus. Persons skilled in the art will appreciate that arterial walls are flexible and change volume in proportion to blood pressure pulses that flow through them. Thus, the waveforms of FIG. 7B also are representations of arterial volume changes in response to a sequence of blood pressure pulses. The two curves in FIG. 7B are representations of the same sequence of arterial pressure pulses. A first arterial pressure curve is labeled to indicate an $I_{HR}$ value indicative of absorption of red light at the maximum (highest) arterial volume and to indicate an $I_{LR}$ value indicative of absorption of red light at the minimum (lowest) arterial volume. A second arterial pressure curve is labeled to indicate an $I_{HR}$ value indicative of absorption of IR light at the maximum (highest) arterial volume and to indicate an $I_{LR}$ value indicative of absorption of IR light at the minimum (lowest) arterial volume.

Figure 8A:
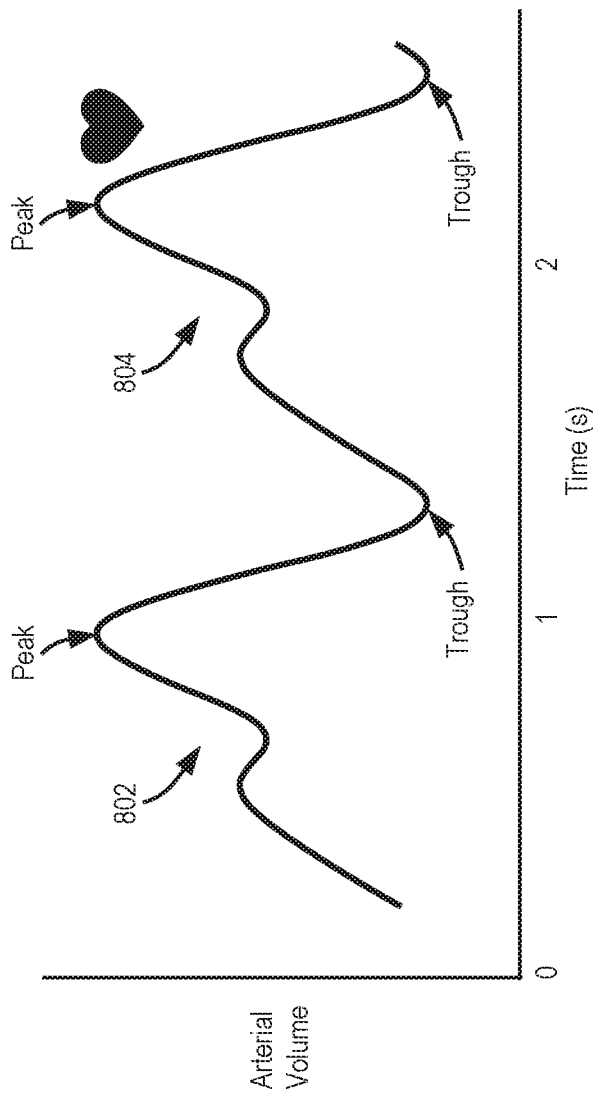
FIGS. 8A-8B are illustrative waveforms representing evolution of arterial volume during a sequence of blood pressure pulses within an artery (FIG. 8A) and an alternating sequence of current values that flow within the red LED and IR LED (FIG. 8B) in accordance with some embodiments.
Figure 8B:
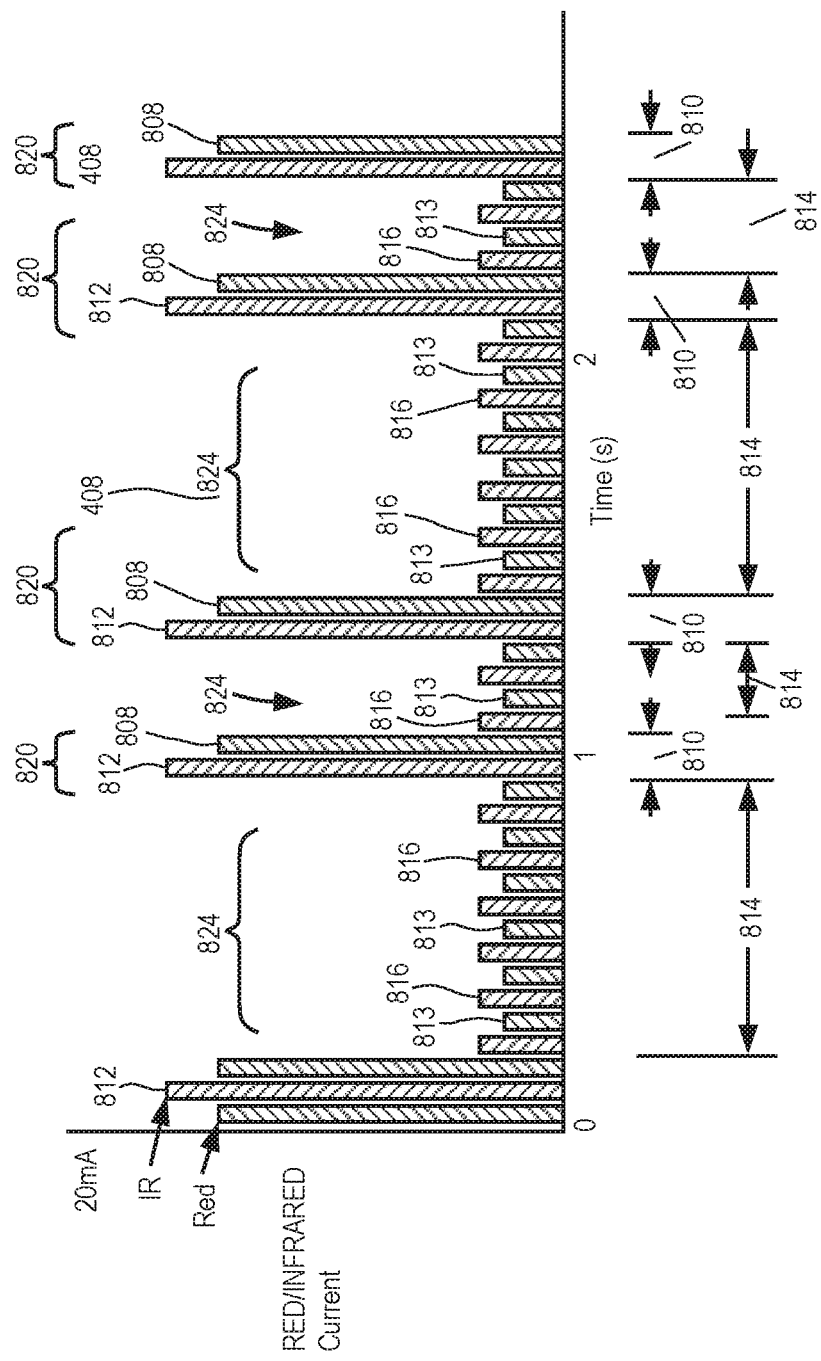

Still referring to FIGS. 7A-7B, it will be appreciated that when the pressure/volume is at a local minimum, the current within the photodetector 604 will be at a local maximum. This is because when the pressure is at a minimum, the arterial volume is smaller so there is less "tissue" for the light to pass through and hence less of the light is absorbed FIGS. 8A-8B are illustrative waveforms 802, 804 representing evolution of arterial volume during a sequence of blood pressure pulses within an artery (FIG. 8A) and an alternating sequence of current values 806 that flow within the red LED and IR LED (FIG. 8B) to alternatingly turn on the red LED and turn on the IR LED at different current magnitude levels during the heart pulse sequence in accordance with some embodiments. The sensor system 600 functions as a SpO2 sensor during the occurrence of arterial volume waveform peaks and troughs. A first pattern of higher current level pulses 820 is provided to the red LED 606-1 and the IR LED 606-2 during the occurrence of arterial volume waveform peaks and troughs. A second pattern of lower current level current pulses 824 is provided to the red LED 606-1 and the IR. LED 606-2 between occurrences of arterial volume waveform maxima/minima. The first pattern of current pulses 820 dissipates more power than the second pattern of current pulses 824.

The first pattern of pulses 820 includes a sequence of first higher value current pulses 808 and a sequence of second higher value current pulses 812. The sequence of first higher value current pulses 808 is provided during first time intervals 810 that encompass occurrences of maximum (peak) and minimum (trough) arterial volume. Each first higher value current pulse turns on the red LED 606-1 for the duration of the pulse. The sequence of second higher value current pulses 812 is provided during the first time intervals 810. Each second higher value current pulse turns on the IR LED 606-2 for the duration of the pulse. The first and second higher current value pulses are time-interleaved so that the red LED 606-1 and the IR LED 606-2 take turns, or alternate, turning on to produce an alternating sequence of higher intensity red light pulses and higher intensity IR light pulses. The first and second higher value currents that alternate between flowing within the red LED 606-1 and within the IR LED 606-2 during the occurrence of arterial volume waveform peaks and troughs, to cause them to take turns emitting higher intensity red light and higher intensity IR light. The emission of high intensity red and IR light during the occurrence of arterial volume waveform maxima and minima ensure high SNR and accurate SpO2 measurements.

Between occurrences of arterial volume waveform peaks and troughs, the sensor system 600 functions as an arterial volume sensor that tracks evolution of arterial volume in response to a heartbeat so as to predict subsequent occurrences of arterial maxima and minima to be evaluated through SpO2 sensing, More particularly, absorbance of the artery is tracked since absorbance is indicative of artery's volume, which is indicative of the stage of evolution of a pressure pulse passing through it. In some embodiments, the sensor system 600 functions as a PPG sensor between peaks and troughs. In general, less light intensity is used for PPG capture for indicative purposes than is used for SPO2 measurements. Therefore, lower value current can be used for arterial volume tracking determinations than is required for accurate SpO2 measurement.

The second pattern of pulses 824 includes a sequence of first lower value current pulses 813 and a sequence of second lower value current pulses 816. A sequence of first lower value current pulses 813 are provided during second time intervals 814 that fall outside the portions of the arterial volume waveform that encompass occurrences of maximum (peak) and minimum (trough) arterial volume, Each first lower value current pulse 813 turns on the red LED 606-1 for the duration of the pulse. A sequence of second lower value current pulses 816 are provided during the second time intervals 814. Each second lower value current pulse 816 turns on the IR LED 606-2 for the duration of the pulse. The first and second lower current value pulses are time-interleaved so that the red LED 606-1 and the IR LED 606-2 take turns, or alternate, turning on to produce an alternating sequence of lower intensity red light pulses and lower intensity IR light pulses, The use of lower current values during arterial diameter tracking conserves battery power. Moreover, tracking of the pulse wave alone, without making SpO2 measurement, can be achieved using, one of the Red or IR LEDs, since Red and IR LED measurements are used in combination to determine peaks and valleys during SpO2 determinations, but both measurements are not required to track the pulse wave alone.

The red LED 606-1 and the IR LED 606-2 are turned on alternately so as to avoid mixing of red light and IR light incident upon the photodiode 608. The current pulses ordinarily are short enough in duration to permit filtering out of background ambient light. Moreover, the time-interleaved first higher value current pulses and second higher value current pulses may be provided tens or hundreds of times during each of the first time intervals 810. Likewise, the time-interleaved first lower value current pulses and second lower value current pulses may be provided tens or hundreds of times during each of the second time intervals 814. Thus, the red LED 606-1 and the IR. LED 606-2 may he turned on hundreds or thousand times during each blood pressure pulse, for example.

Figure 9:
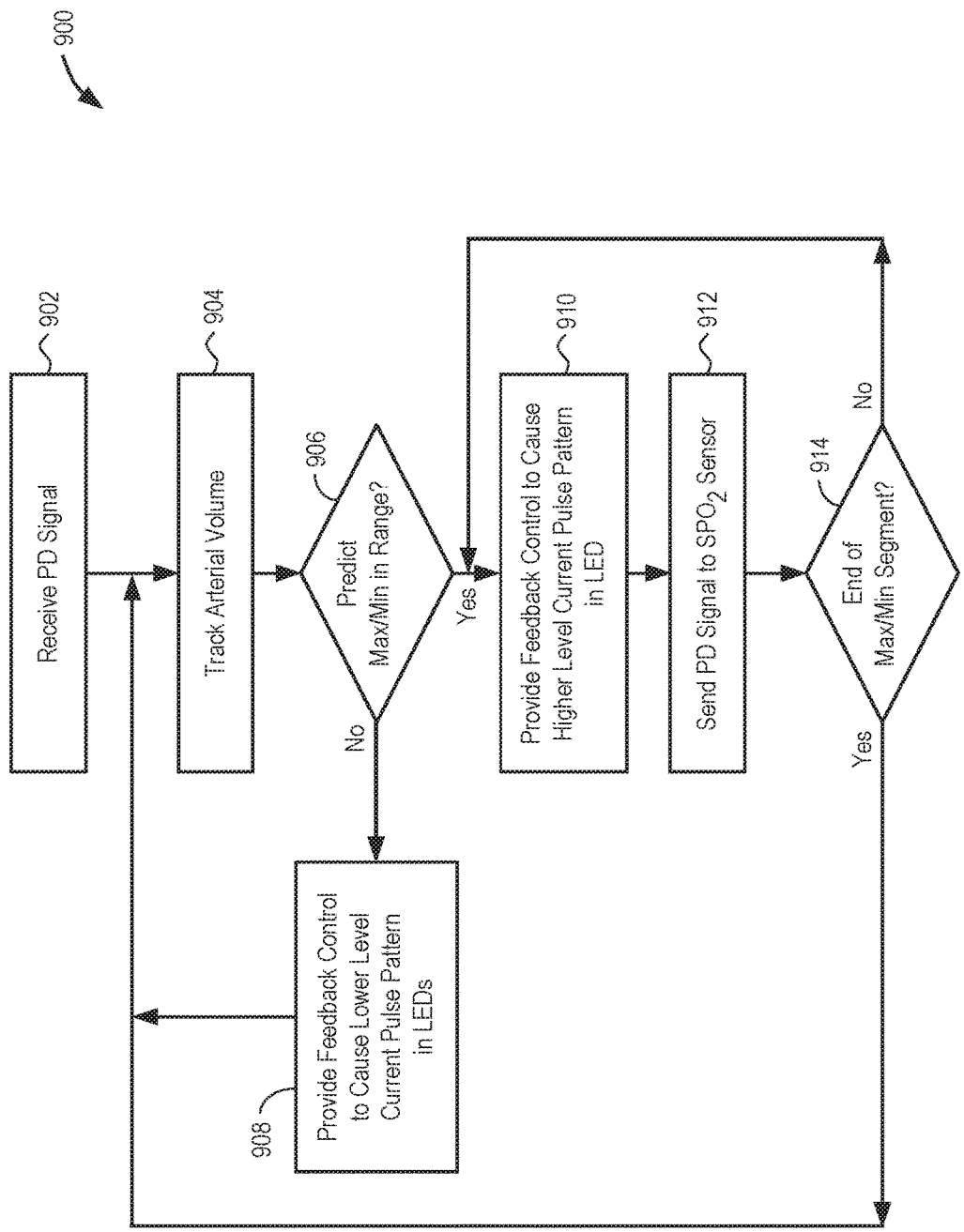
FIG. 9 is an illustrative flow diagram representing a process to determine electrical current consumption of first and second LED light sources during evolution of arterial volume waveform in accordance with some embodiments.

FIG. 9 is an illustrative flow diagram representing a process 900 to determine the pattern of current pulses that flow within the red LED 606-1 and their LED 606-2 in accordance with some embodiments. The blocks in the diagram represent configuration of the processor 624 to perform acts corresponding to the blocks. Computer program code to configure the processor 624 is stored in the storage device 626. Block 902 configures the processor 624 to receive the signal on line 602 that indicates present light intensity incident upon the photodetector 608. Signal values received on line 602 can be stored in storage device 626. Block 904 configures the processor 624 to use the received light intensity information to predict successive occurrences of maximum and minimum arterial volume. More particularly, block 904 configures the processor 624 to perform processing to track evolution of arterial volume based upon the received light intensity information. More particularly, in some embodiments, block 904 configures the processor 624 to perform PPG processing that tracks reflectivity of an artery volume based upon the received light intensity information. Arterial reflectivity is indicative of stage of evolution of arterial volume during passage of a blood pressure pulse through it. An artery exhibits a characteristic arterial volume evolution and exhibits a corresponding evolution of arterial reflectivity that is indicative of the stage of volume evolution during passage of a pressure pulse through it. Block 904 configures the processor 624 to use the intensity information to track artery reflectivity to thereby track the evolution of the artery's volume during passage of blood pressure pulses.

Prediction block 906 configures the processor 624 to predict times of occurrence of the first time intervals 810 during which first and second higher current value pulses 808, 812 are to be provided. The prediction block 906 can be configured in alternate ways to use different criteria to predict times of occurrence of arterial volume maxima and minima. For example, the prediction can be based upon an arterial volume threshold, based upon an arterial volume waveform morphology, based upon PPG signal model, based upon time series or based upon an external trigger.

In response to a determination by block 906 that the tracked arterial volume presently is not within the prescribed range of an arterial volume maximum or minimum, block 908 configures the processor 624 to provide a feedback control signal on line 611 to provide the time-interleaved sequences of first lower value current pulses 812 and second lower value current pulses 816 to the red LED 606-1 and to the IR LED 606-2, respectively. Accordingly, the red LED 606-1 and the IR LED 606-2 consume lower power while emitting lower intensity light During arterial volume tracking between volume maxima and volume minima. Control next flows back to block 904 which continues tracking arterial volume.

In response to a determination by block 906 that the tracked arterial volume presently is within the prescribed range of an arterial volume maximum or minimum, block 910 configures the processor 624 to provide a feedback control signal on line 611 to cause the driver circuit 612 to provide the time-interleaved sequences of first higher value current pulses 808 and second higher value current pulses 812 to the red LED 606-1 and to the IR LED 606-2, respectively. Accordingly, the red LED 606-1 and the IR LED 606-2 consume higher power while emitting higher intensity light. Control next flows back to block 912, which configures the processor 624 to use light intensity information received on line 620, while the first and second higher value pulses are provided to the red LED 606-1 and to the IR LED 606-2, to perform $SpO_2$ evaluations according to formulation (1) above. Decision block 914 next determines whether the arterial volume has evolved past the present maximum/minimum segment. In accordance with some embodiments, the prediction block 906 determines a predicted time when the maximum/minimum segment will pass. The predicted time can be saved in the storage device 626. In accordance with some embodiments, higher intensity LED light is stimulated during a time interval that spans a sufficient amount before and after the actual maximum and minimum volume to obtain sufficient intensity data to make accurate $SpO_2$ determinations. In response to a determination by block 914 that arterial volume has not evolved past the present maximum/minimum segment, control flows to block 910. In response to a determination by block 914 that arterial volume has evolved past the present maximum/minimum segment, control flows to block 904.

Figure 10A:
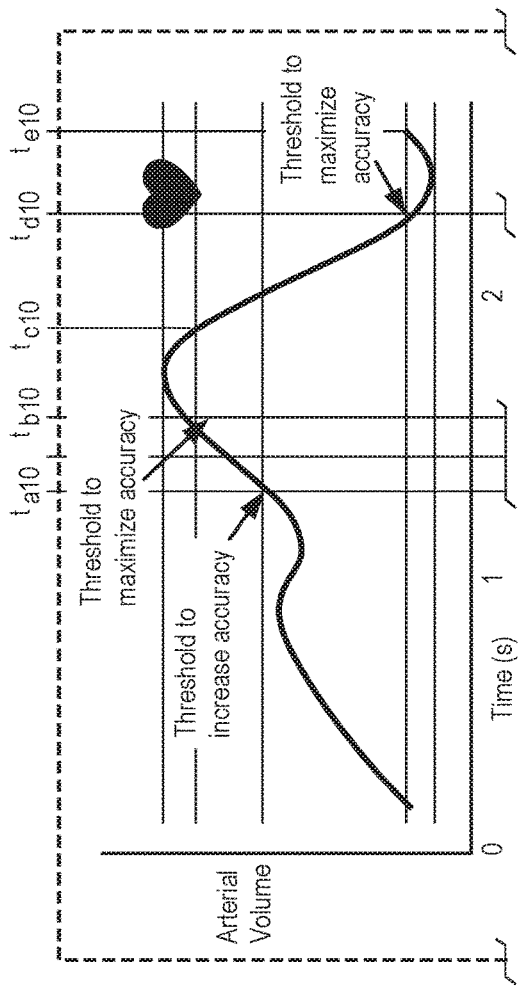
FIGS. 10A-10B are illustrative drawings representing arterial pressure during a sequence of blood pressure pulses within an artery (FIG. 10A) and an alternating sequence of LED current values (FIG. 10B) that pulse at different frequencies in response to an arterial volume threshold value in accordance with some embodiments.
Figure 10B:
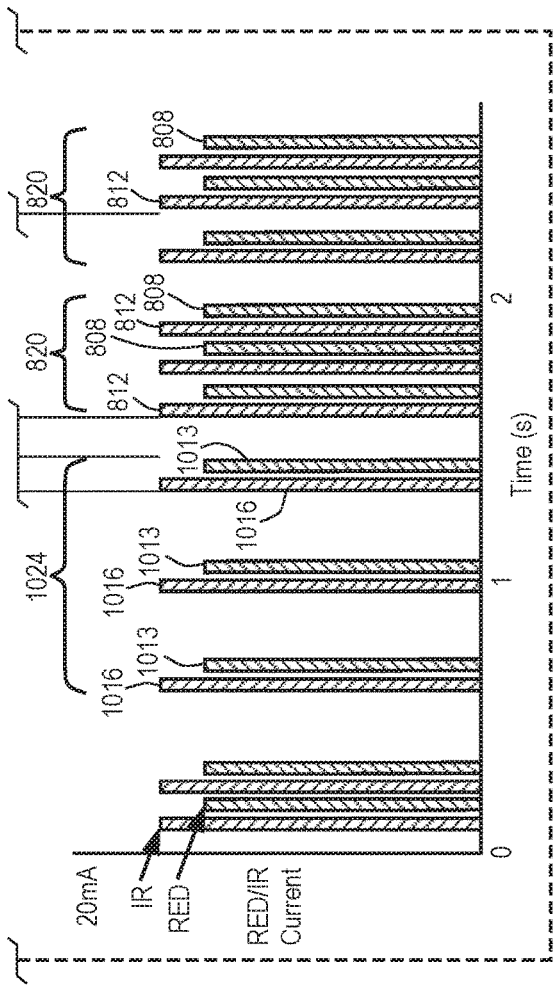

FIGS. 10A-10B are illustrative drawings representing arterial pressure during a sequence of blood pressure pulses within an artery (FIG. 10A) and an alternating sequence of LED current values (FIG. 10B) that pulse at different frequencies in response to an arterial volume threshold value in accordance with some embodiments. It will be appreciated that a pulse oximeter sensor system (not shown) that produces the pulse patterns of FIG. 10B does not require higher and lower level current value current sources. In accordance with some embodiments, prediction block 906 monitors a tracked arterial volume waveform to predict occurrences of arterial volume maximums and minimums based upon an arterial volume threshold value. In response to the light intensity signal on line 620 signal indicating that the arterial volume waveform has reached a prescribed threshold volume, the prediction block 906 predicts a time of occurrence of a next corresponding maximum or minimum. For example, in some embodiments, in response to the arterial volume waveform indicating an arterial volume $V_a$ at time $Ta_{10}$, the prediction block 906 predicts a start of a maximum value interval at time $T_{b10}$, and an end of the maximum value interval at time $T_{c10}$ and also predicts a start of a minimum value interval at time $T_{d10}$ and an end of the minimum value interval at time $T_{e10}$. In accordance with some embodiments, the maximum and minimum time intervals are selected to be long enough to ensure higher intensity red and IR light illumination of the artery for a sufficient time duration for an accurate oxygenation level measurement. Referring again to FIG. 9, in response to a determination by prediction block 906 that the threshold has not been reached, control flows to module 908. In response to a determination by prediction block 906 that the threshold has been reached, control flows to module 910. In accordance with some embodiments, the threshold arterial volume $V_a$ can be a fixed value or it can be changed based upon evolution of the arterial volume waveform. That is, the threshold may be adaptive.

FIGS. 11A-11B are illustrative drawings representing arterial pressure during a sequence of blood pressure pulses within an artery (FIG. 11A) and an alternating sequence of LED current values (FIG. 11B) that pulse at different at different pulse rate frequencies in response to an arterial volume waveform morphology in accordance with some embodiments. An arterial volume waveform includes certain characteristic features. For example, a longer phase portion of the waveform typically includes a bump or change in slope. In accordance with some embodiments, prediction block 906 monitors a tracked arterial volume waveform to predict occurrences of arterial volume maximums and minimums based upon morphology of the arterial volume waveform. In response to the light intensity signal on line 620 indicating that the arterial volume waveform has reached a prescribed morphology, the prediction block 904 predicts a time of occurrence of a next corresponding maximum or minimum. For example, in response to the arterial volume waveform reaching the bump X at $T_{a11}$, the prediction block 904 predicts a start of a maximum value interval at time $T_{b11}$ and an end of the maximum value interval at time $T_{c11}$ and also predicts a start of a minimum value interval at time $T_{d11}$ and an end of the minimum value interval at time $T_{e11}$. Referring again to FIG. 9, in response to a determination by prediction block 906 that the morphology has not been detected, control flows to module 908. In response to a determination by prediction block 906 that the morphology has been detected, control flows to module 910.

In some embodiments, each of the pulses represented as 1016 and 1013, for example, actually is a composite of a plurality of consecutive short constituent pulses. Increasing the number of constituent pulses used to create a composite pulse typically reduces noise but increase power dissipation. In some embodiments, the number of constituent pulses used to create a composite pulse varies with position of the composite pulse 1016, 1013 in the heartbeat cycle, with a larger number of short constituent pulses occurring within composite pulses that occur at peaks and troughs.

Referring to both FIG. 10B and FIG. 11B, the first pattern of current pulses 820, which includes time-interleaved first and second higher value current pulses 808, 812, are produced in the red LED and in the IR LED, respectively, during occurrences of arterial volume waveform maxima and minima. A second lower frequency pattern of current pulses 1024 is provided to the red LED 606-1 and the IR LED 606-2 between occurrences of arterial volume waveform maxima/minima. The second pattern of current pulses 1024 includes time-interleaved higher value third and fourth current pulses 1013, 1016 that are produced in the red LED and in the IR LED, respectively, between occurrences of arterial volume waveform maxima/minima. Although the current values of the third and fourth pulses 1013, 1016 are the same as those of the first and second current pulses, the third and fourth pulses 1013, 1016 are produced less frequently, and therefore, are sparser. Thus, second pattern of current pulses 820 consumes more power than the second pattern of current pulses 1024, which conserves battery power through the use of less frequent pulses between the maximal/minima. This contrasts with the second pattern of current pulses 824 of FIG. 8B which conserves battery power through use of lower current level, pulses 813, 816 between maxima/minima as in the.

In some embodiments, sparse sampling may be performed in combination with reduced current levels between peaks and valleys. For example, between peaks and valleys, current intensity may be reduced and time between light pulses may be increased, When a next peak or valley is close, as determined based upon prediction or based upon a fixed delay until, the current intensity and light pulse frequency both can be increased.

In some embodiments, the prediction block 906 predicts occurrences of maximum and minimum waveform segments based upon a model of a characteristic PPG signal. See, Stochastic Modeling of the PPG Signal: A Synthesis-by-Analysis Approach with Applications, Diego Martin-Martinez, Pablo Casaseca-de-la-Higuera, Marcos Martin-Fernandez, Carlos Alberola-Lopez, *IEEE Trans on Biomed Eng*, V. 60, N. 9, September, 2013. The prediction block 906 matches PPG signal samples obtained at time intervals in between arterial volume waveform maxima and minima to the model to predict subsequent occurrences of waveform maxima and minima.

In some embodiments, the prediction block 906 predicts occurrences of maximum and minimum waveform segments based upon duration of prior occurrences of maxima and minima. The prediction block 906 determines times of occurrence of previously maximum and minimum segments of the arterial volume waveform to create a time series indicative of time intervals between maximums and minimums. Time intervals that encompass successive later occurring maxima and minima are determined based upon the times of occurrence of prior maxima and minima. A number of other approaches can be used to predict future maxima and minima based upon times of occurrence of prior maxima and minima. For example, the time intervals between previous maxima and minima can be used to predict time intervals between subsequent maxima and minima. The average of the previous N time intervals can be used to predict the next to occur maximum or minimum. A weighted (exponential) average of the previous N intervals can be used to predict the next to occur maximum or minimum so that the closest ones have more relevance than older. A linear prediction algorithm can be used (similar to above but weights are self-tuned. to reduce the error in the prediction). Moreover, an activity monitor (accelerometer) can be used to detect whether a patient is moving or relaxed. If moving (or changing move pattern) more weight may be given to the last values of a time series and ignore 'older' beat durations as the heart should be "resynchronizing" to the new demands. A PLL lock strategy can be employed that "locks" to the frequency of the heartbeat. For example, the LEDs are turned in with the higher current level at about 20 degrees in advance of the anticipated peak. If the peak happens earlier or later than anticipated, then the turn on time is amended the turn on time for the next peak. In that manner, a heartrate which changes over time does not result in missed maxima or minima.

In some embodiments, the prediction block 906 predicts occurrences of maximum and minimum waveform segments based upon other external sensors. For example, in some embodiments, the prediction block 906 receives a trigger signal in response to an ECG monitor detecting an occurrence of an R wave in a heartbeat evolution. The trigger signal is used to predict a time of occurrence of next arterial waveform maximum and minimum.

The foregoing description and drawings of embodiments in accordance with the present invention are merely illustrative of the principles of the invention. For example, a broadband light source may be provided that emits light of two different wavelengths and a photodetector may be provided that filters received light to detect the intensity of light of each of the two wavelengths. More particularly, for example, a single LED may be provided that emits light in both the Red and IR bands, and one or more photodetectors may be provided that filter the received light to determine intensity of light received at each wavelength. Therefore, it will be understood that various modifications can be made to the embodiments by those skilled in the art without departing from the spirit and scope of the invention, which is defined in the appended claims.

The invention claimed is:

1. A blood oxygenation sensor system comprising:
one or more light sources powered by a current source;
a light sensor to produce a sensor signal having a magnitude that is indicative of intensity of light incident upon the light sensor; and
a processor configured to:
predict times of occurrence of one or more first time intervals in which arterial volume at a tissue site is at one of a maximum and a minimum, wherein the prediction is based at least in part on information received from the sensor during one or more second time intervals when the arterial volume at the tissue site is between the maximum and minimum; and
control the current source to provide higher power-dissipation current pulses to the one or more light sources during the first time intervals, and to provide lower power-dissipation current pulses to the one or more light sources during the second time intervals.

2. The sensor system of claim 1, wherein the processor is configured to determine a blood oxygenation level based at least in part upon a magnitude of the sensor signal during the first time intervals,
wherein light incident upon the light sensor during the first time intervals is produced by the light sources in response to the higher power-dissipation current pulses, and
wherein the light incident upon the light sensor during the first time intervals has passed through the tissue site.

3. The sensor system of claim 1, wherein the processor is configured to determine a blood oxygenation level as a function of a magnitude of the sensor signal in response to light incident upon the light sensor during the first time intervals and an average magnitude of the sensor signal in response to light incident upon the light sensor during intervals that include the higher power-dissipation current pulses and the lower power-dissipation current pulses provided to the one or more light sources.

4. The sensor system of claim I, wherein the light sensor includes a photodiode and the one or more light sources comprises a red LED and an IR LED.

5. The sensor system of claim 1, further comprising a current level driver circuit including at least one current source configured to alternately provide current to different ones of the light sources, wherein the current level driver circuit is configured to provide the current at a selectable current level.

6. The sensor system of claim 1, wherein the processor is configured to predict times of occurrence of one or more first time intervals in which arterial volume at the tissue site is at one of the maximum and minimum based at least in part upon a magnitude of the sensor signal indicating that the arterial volume at the tissue site has reached a threshold volume.

7. The sensor system of claim 1, wherein the processor is configured to predict times of occurrence of one or more first time intervals in which arterial volume at the tissue site is at one of the maximum and minimum based at least in part upon a morphology of an arterial volume waveform as determined using the sensor signal.

8. The sensor system of claim 1, wherein the processor is configured to predict times of occurrence of one or more first time intervals in which arterial volume at the tissue site is at one of the maximum and minimum based at least in part upon one or more of (1) a portion of an ECG signal and (2) a linear prediction based upon previous times of occurrence of maximums and minimums.

9. The sensor system of claim 1, wherein the processor is configured to control the current source to:
provide the higher power-dissipation current pulses at a first frequency to the light sources during the first time intervals, and
provide the lower power-dissipation current pulses at a lesser second frequency to at least one of the light sources during second outside of the first time intervals.

10. The sensor system of claim 1, wherein the processor is configured to control the current source to:
provide the higher power-dissipation current pulses at a first current level to the light sources during the first time intervals, and
provide the lower power-dissipation current pulses with a lower at a lesser second current level to at least one of the light sources outside of the first time intervals.

11. The sensor system of claim 1, wherein the processor is configured to control the current source to:
provide the higher power-dissipation current pulses at a greater first current level and with a greater first frequency to the light sources during the first time intervals, and
provide the lower power-dissipation current pulses at a lesser second current level and with a lesser second frequency to the light sources outside of the first time intervals.

12. The sensor system of claim 1 further including:
a converter circuit to convert the sensor signal from the light sensor to a light source voltage signal; and
an ADC circuit configured to convert the light source voltage signal to a digital signal;
wherein the processor is configured to predict times of occurrence and to control the current source in response to the digital signal.

13. The sensor system of claim 1, wherein the processor produces a digital feedback signal to control the current source in response to the digital feedback signal;

wherein the sensor system further includes a DAC circuit coupled to convert the digital feedback signal to an analog feedback signal; and wherein the current source is configured to alternatively provide current o first and second light sources in response to the analog feedback signal.

14. For use with a blood oxygenation sensor that includes one or more light sources and a photodiode, a method comprising:

producing first higher power-dissipation current pulses in drive circuitry for the one or more light sources during first time intervals while an arterial volume at a tissue site is at or near a maximum and during first time intervals while the arterial volume at the tissue site is at or near a minimum;

producing second lower power-dissipation current pulses in the drive circuitry for the one or more light sources during second time intervals while the arterial volume at the tissue site is between the minimum and maximum: and predicting times of occurrence of arterial volume maximums and minimums based at least in part upon current stimulated in the photodiode in response to light that is emitted by the one or more light sources in response to the second current pulses and that passes through the tissue site before reaching the photodiode.

15. The method of claim 14, wherein producing the first higher power-dissipation current pulses includes producing pulses at a higher frequency during the first time intervals; and wherein producing the second lower power-dissipation current pulses includes producing pulses at a lower frequency during the second time intervals.

16. The method of claim 14, wherein producing the first higher power-dissipation current pulses includes producing pulses with a higher current level during the first time intervals; and wherein producing the second lower power-dissipation current pulses includes producing pulses with a lower current level during the second time intervals.

17. The method of claim 14, further comprising determining a blood oxygenation measurement based at least in part upon current stimulated in the photodiode in response to light that is emitted by the one or more light sources in response to the first current pulses and that passes through the tissue site before reaching the photodiode.

18. A device for use in evaluating a blood oxygen level of a patient, the device comprising:

a drive circuit configured to provide power signals to one or more light sources; and a processor circuit configured to:

receive information from a first sensor about a vessel volume of the patient over time, the information indicating an intensity of light incident upon the first sensor from the one or more light sources;

using the information from the first sensor about the vessel volume, control the drive circuit to provide first power signals to the one or more light sources during first intervals when the vessel volume is at or near a maximum or a minimum volume, and control the drive circuit to provide second power signals to the one or more light sources during second intervals when the vessel volume is at an intermediate volume, wherein the first power signals have at least one of a greater magnitude characteristic and a greater frequency characteristic relative to the second power signals;

predict times of occurrence of the first intervals based on information received from the first sensor during the second intervals, and control the drive circuit to provide the power signals based on the predicted times of occurrence of the first intervals.

19. The device of claim 18, wherein the processor is configured to determine a blood oxygen level for the patient based upon information from the first sensor acquired during the first intervals.

* * * * *

UNITED STATES PATENT AND TRADEMARK OFFICE
CERTIFICATE OF CORRECTION

PATENT NO. : 10,582,887 B2
APPLICATION NO. : 15/072961
DATED : March 10, 2020
INVENTOR(S) : O'Donnell et al.

It is certified that error appears in the above-identified patent and that said Letters Patent is hereby corrected as shown below:

In the Claims

In Column 14, Line 1, in Claim 4, delete "claim I," and insert --claim 1,-- therefor In Column 15, Line 5, in Claim 13, delete "o" and insert --to-- therefor In Column 15, Lines 18-19, in Claim 14, delete "maximum:" and insert --maximum;-- therefor Signed and Sealed this
Fifteenth Day of September, 2020

Andrei Iancu
*Director of the United States Patent and Trademark Office*